United States Patent
Miller et al.

(10) Patent No.: US 6,213,944 B1
(45) Date of Patent: Apr. 10, 2001

(54) ULTRASONIC DIAGNOSTIC IMAGING SYSTEM WITH A DIGITAL VIDEO RECORDER WITH VISUAL CONTROLS

(75) Inventors: Edward A. Miller, Everett, WA (US); Philip V. Jones, Paramus, NJ (US); Jeffrey W. Burton, Bothell, WA (US)

(73) Assignee: ATL Ultrasound, Inc., Bothell, WA (US)

( * ) Notice: Subject to any disclaimer, the term of this patent is extended or adjusted under 35 U.S.C. 154(b) by 0 days.

(21) Appl. No.: 09/314,470

(22) Filed: May 18, 1999

Related U.S. Application Data

(60) Provisional application No. 60/123,040, filed on Mar. 5, 1999.

(51) Int. Cl.[7] .................................................. A61B 8/00
(52) U.S. Cl. ................................................................ 600/437
(58) Field of Search ..................... 600/443–447, 600/437; 364/11, 518; 358/98, 110, 403; 382/254

(56) References Cited

U.S. PATENT DOCUMENTS

| | | |
|---|---|---|
| 3,988,778 | 10/1976 | Swenson . |
| 4,412,249 * | 10/1983 | Carmen ................................. 358/112 |
| 5,124,789 * | 6/1992 | Hiyama et al. ........................ 358/98 |
| 5,152,290 | 10/1992 | Freeland . |
| 5,211,169 | 5/1993 | Freeland . |
| 5,474,073 | 12/1995 | Schwartz et al. . |
| 5,583,566 | 12/1996 | Kanno et al. . |
| 5,603,323 * | 2/1997 | Pflugrath et al. ..................... 600/437 |
| 5,619,995 | 4/1997 | Lobodzinski . |
| 5,680,129 | 10/1997 | Weinberger et al. . |
| 5,795,297 * | 8/1998 | Diagle .................................. 600/447 |
| 5,920,317 | 7/1999 | McDonald . |

FOREIGN PATENT DOCUMENTS

WO 82/01784   5/1982   (WO) .

OTHER PUBLICATIONS

Davis, Dobutamine Stress Echo, Stress Echocardiography (Krannert Institue of Cardiology, 1989).

* cited by examiner

Primary Examiner—Marvin M. Lateef
Assistant Examiner—Ali M. Imam
(74) Attorney, Agent, or Firm—W. Brinton Yorks, Jr.

(57) ABSTRACT

A digital video recorder is provided which provides digital storage of realtime ultrasonic image sequences, replacing the conventional VCR with a recorder which does not degrade digital ultrasound images by analog conversion and recording. The digital video recorder is operated by softkey controls in a displayed toolbar which are familiar to a VCR user. The virtual controls of the toolbar are selected by a video pointing device to stop, start, control replay speed, and skip to various points in a realtime ultrasonic image sequence which was stored by the digital video recorder.

28 Claims, 4 Drawing Sheets

ULTRASONIC DIAGNOSTIC IMAGING SYSTEM WITH A DIGITAL VIDEO RECORDER WITH VISUAL CONTROLS

This application claims the benefit of U.S. Provisional application No. 60/123,040, filed Mar. 5, 1999.

This invention relates to ultrasonic diagnostic imaging systems and, in particular, to ultrasonic diagnostic imaging systems which digitally store and retrieve ultrasonic image information.

One of the advantages that diagnostic ultrasound has had over many other diagnostic imaging modalities is the ability to produce realtime images. The advantage has been especially significant in echocardiography where the physiology of a continually moving organ, the heart, are the subject of study. Realtime imaging has been a virtual necessity in echocardiography as compared with abdominal and obstetrical applications where the tissues and organs being studies are stationary and may be readily examined by static imaging. Echocardiologists, like other practitioners of diagnostic ultrasound, make records of their ultrasound examinations for subsequent diagnosis, review, and comparison. Since echocardiography studies use realtime ultrasonic imaging, they are conventionally recorded on videotape with a VCR, rather than being recorded statically on film or as photographic prints. A VCR has been an essential accessory for an echocardiography system for many years.

Over time ultrasonic imaging systems have become increasingly digital, whereas VCRs have remained recorders of analog video signals. Thus it has been necessary to convert the digital ultrasound images produced by the digital scan converter of an ultrasound system into modulated and synchronized video signals before the images can be recorded by a VCR. This conversion does not contribute to the quality of the image, and often is detrimental to image resolution. This detriment has been viewed as one which must be accepted, however, since the VCR has traditionally provided the only efficient means for recording many minutes of live, realtime echocardiographic image sequences.

The present invention is directed to replacing the VCR with an all-digital means for storing realtime ultrasonic image sequences, a true digital video replacement of the VCR. The present invention allows many minutes of realtime ultrasonic image sequences to be stored on a high capacity digital storage medium such as a hard disk, CD-RW, magneto-optical or floppy disk. In a preferred embodiment the user has the ability to control the degree of compression of the image data. A high degree of compression enables an increased number of images to be stored on a given digital storage medium. A constructed embodiment of the present invention provides virtual VCR controls whereby the user can operate the digital video recorder similar to the manner in which he is accustomed to operating a VCR.

Figure 1:
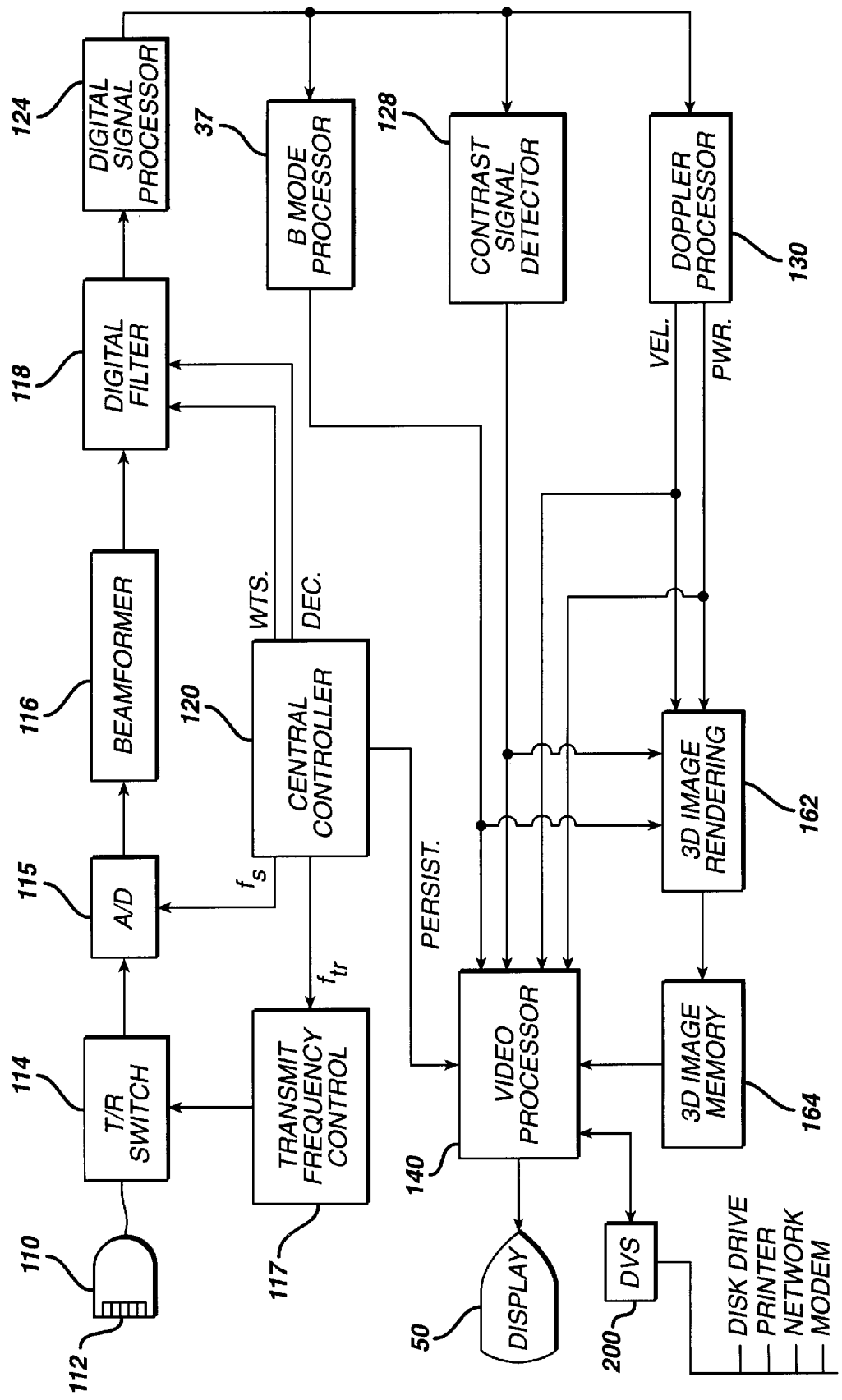
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. A central controller 120 commands a transmit frequency control 117 to transmit ultrasonic scanning beams of a desired transmit frequency band. The parameters of the transmit frequency band, $f_{tr}$, are coupled to the transmit frequency control 117, which causes the transducer 112 of ultrasonic probe 110 to transmit the desired ultrasonic waves. The array transducer 112 of the probe 110 transmits ultrasonic energy and receives echoes returned in response to this transmission. In FIG. 1 these echoes are received by the transducer array 112, coupled through the T/R switch 114 and digitized by analog to digital converters 115. The sampling frequency $f_s$ of the A/D converters 115 is controlled by the central controller. The desired sampling rate dictated by sampling theory is at least twice the highest frequency $f_c$ of the received passband. Sampling rates higher than the minimum requirement are also desirable.

The echo signal samples from the individual transducer elements are delayed and summed by a digital beamformer 116 to form coherent echo signals. The digital coherent echo signals are then filtered by a digital filter 118. In this embodiment, the transmit frequency $f_t$ is not tied to the receiver, and hence the receiver is free to receive a band of frequencies which is different from the transmitted band. The digital filter 118 can thus pass harmonic frequency signals of a fundamental transmit band of frequencies. A preferred technique for separating harmonic signals is described in U.S. Pat. Nos. 5,706,819 and 5,951,478. The received echo signals may then be further processed, for instance by processing to remove artifacts such as speckle, by a digital signal processor 124.

The echo signals are detected and processed by either a B mode processor 37 or a harmonic signal detector 128 for display as a two dimensional ultrasonic image on the display 50. The echo signals are also coupled to a Doppler processor 130 for conventional Doppler processing to produce velocity and power Doppler signals which may be used to produce a colorflow or power Doppler 2D image. The outputs of these processors are also coupled to a 3D image rendering processor 162 for the rendering of three dimensional images, which are stored in a 3D image memory 164. Three dimensional rendering may be performed as described in U.S. Pat. No. 5,720,291, and in U.S. Pat. Nos. 5,474,073 and 5,485,842, the latter two patents illustrating three dimensional power Doppler ultrasonic imaging techniques. The signals from the harmonic signal detector 128, the processors 37 and 130, and the three dimensional image signals are coupled to a video processor 140 where they may be selected for two or three dimensional display on an image display 50 as dictated by user selection.

In accordance with the principles of the present invention, the video processor 140 is coupled to a digital video storage (DVS) system 200 which processes digital video signals and audio in realtime for recording, transmission, or reproduction. As FIG. 1 shows, the DVS system is coupled to storage, transmission and reproduction media such as disk drives, printers, networks and modems. The DVS system processes this information while the user is simultaneously observing the realtime image sequence on the display 50. The DVS system also replays recorded digital video information on the display 50 when commanded to do so. The DVS system operates as a digital video recorder which replaces the conventional VCR with a realtime, all-digital recorder and player without the analog conversion degradation of the VCR.

Figure 2:
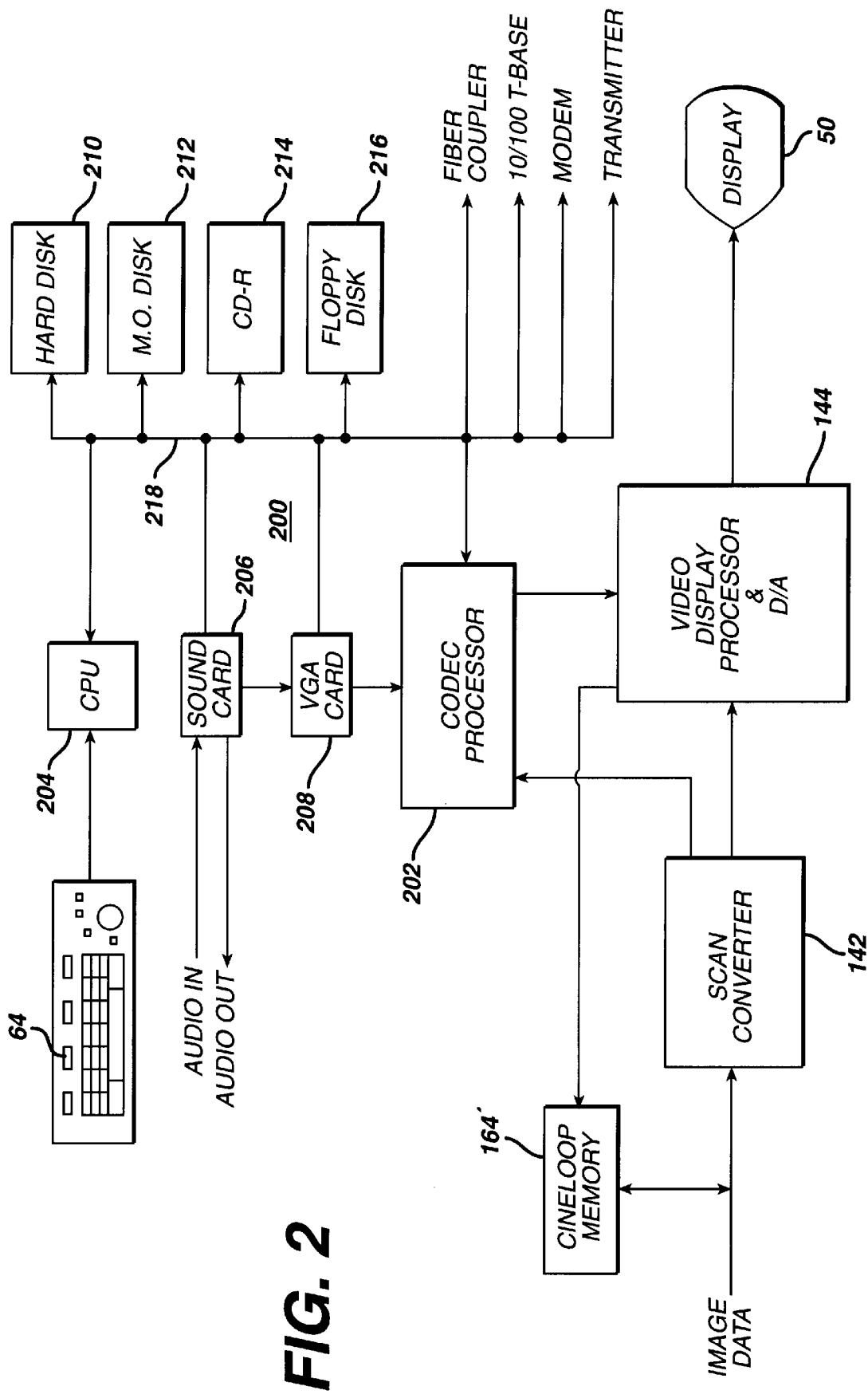
FIG. 2 illustrates in greater detail the digital video storage system and the video processor of the ultrasound system of FIG. 1.

Referring to FIG. 2, portions of the video processor 140, the 3D image memory 164, and the DVS system 200 are shown in greater detail. Digital image data produced by any of the aforementioned processors or detectors is coupled to the input of a digital scan converter 142, which processes and converts received echo information into an ultrasound image of the desired format, e.g., sector-shaped or rectangular. The image data can also be stored in a Cineloop® memory 164'. The Cineloop memory is a random access memory (RAM) temporary storage buffer which can hold a number of still or realtime images for immediate review or processing. For example, a typical Cineloop memory can hold a loop (realtime sequence which is replayed) of 400 images for continual replay and review. At a realtime frame rate of 30 frames per second, the Cineloop memory can hold a twelve second loop, for instance. At lower realtime frame rates, e.g., 15 frames per second, the loop will play for a greater duration. An image or loop stored in the Cineloop memory is replayed through the scan converter and a video display processor & D/A converter 144, which processes the digital video signals into analog video signals with synchronizing pulses for display on a display monitor 50. The Cineloop memory can also receive scan converted digital images by way of the video display processor & D/A 144, which is useful for assembling and storing a 3D image sequence, as explained in the aforementioned U.S. Pat. No. 5,485,842.

In accordance with the principles of the present invention, digital video signals are coupled to a codec (compression/decompression) processor 202 of the DVS system 200. In a constructed embodiment the digital video signals are digital RGB (red, green, blue) signals. The codec processor assembles received images into formats determined by user selected protocols, optionally compresses the image data as selected by the user, and puts the processed data onto a host system bus 218. The data on the host system bus is directed to the desired storage, transmission or reproduction medium by a CPU 204. The data can be stored on nonvolatile digital storage media, including a hard disk 210, a magneto-optical disk 212, a CD-RW disk 214, or a digital disk 216. A preferred digital storage device is one using a high density removable disk media which is capable of holding the data from several ultrasound studies such as an LS 120 floppy disk. The ultrasound data can also be transmitted over a fiber optic network by way of a fiber coupler to printers and other reproduction and storage devices over a 10/100 base-T network connection, by modem, or by wireless transmitter. In a constructed embodiment the DVS system is integrated into the ultrasound system and is operated by the ultrasound system's user interface 64 (keyboard, control keys, trackball, softkeys, and displayed controls and hand controller).

The DVS system 200 includes a conventional computer sound card 206 to digitize and reproduce audio signals such as audio Doppler ultrasound, and a conventional computer VGA card 208 for the processing of ultrasound image graphics such as patient name and image depth markers. Preferably the CPU 204, sound card 206, and VGA card 208 share the same motherboard, and a portion of the host system bus 218 is provided by the motherboard. These modules may be connected to the DVS system by various bus architectures which may be compatible with the specific module. For example, the VGA card may be connected to an AGP bus, the sound card and floppy disk may be connected to an ISA bus, and the hard disk and codec may be connected to a PCI bus, all of which comprise the host system bus.

Figure 3:
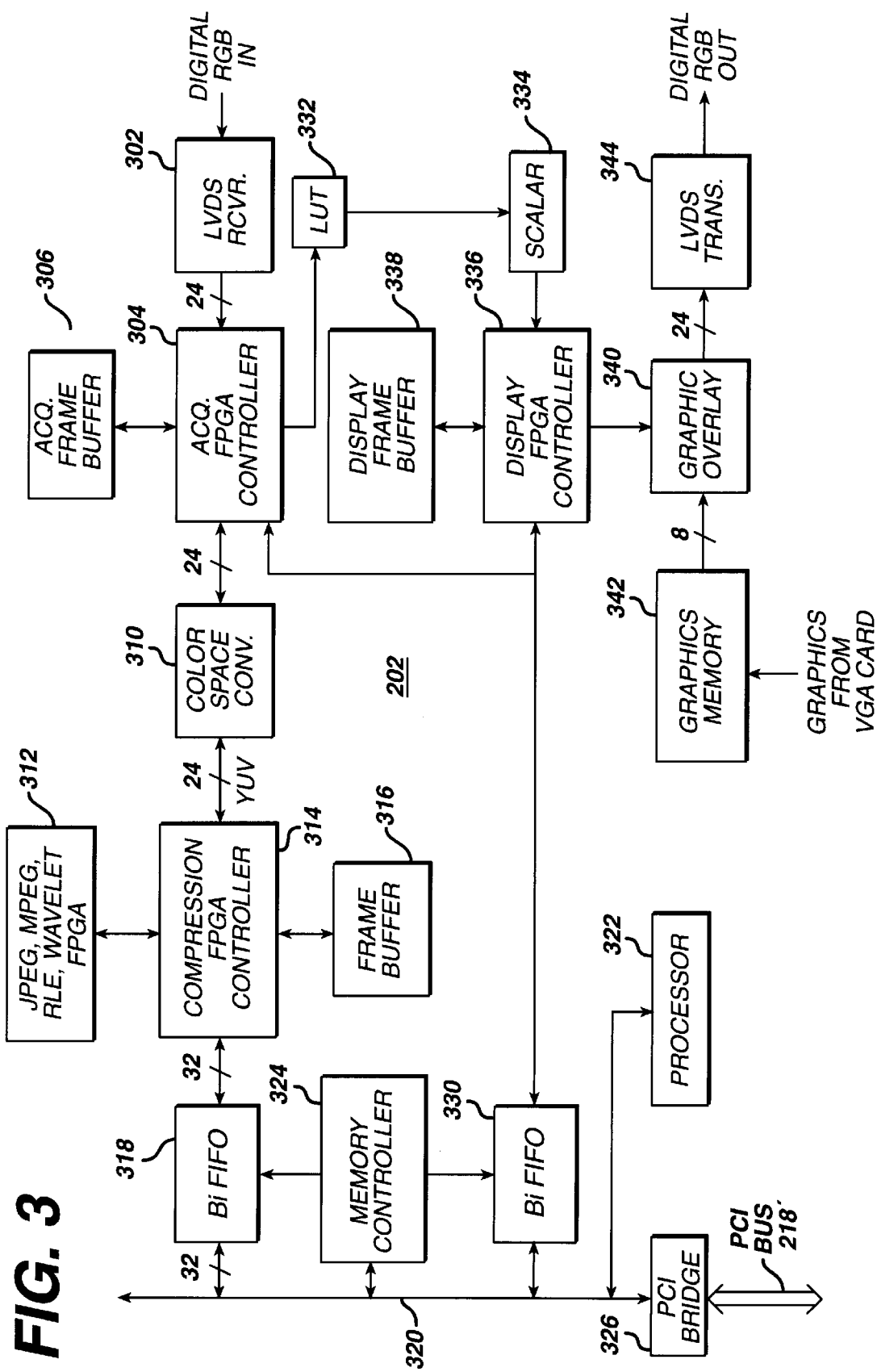
FIG. 3 illustrates in greater detail the codec processor of the digital video storage system of FIG. 2.

Turning to FIG. 3, the codec processor 202 is shown in greater detail. Digital RGB video is received by the processor 202 at the input of an LVDS (low voltage differential signal) receiver 302. At the output of the LVDS receiver 302 the digital RGB signals comprise three bytes (red, green and blue) of eight bits each and in a constructed embodiment are received at a rate of 24.5 MHz for NTSC signals and 29.5 MHz for PAL signals. The digital video signals are then assembled into a full image frame in an acquisition frame buffer 306 under control of an acquisition FPGA (field programmable gate array) controller 304. The acquisition FPGA controller can also crop an incoming image frame so that only a specified region of interest of the full image is retained. The assembled image frame is coupled to a color space converter 310, which converts the 24 bit RGB signals into 24 bit YUV signals. The YUV signals then may be compressed if directed by the user under control of a compression FPGA controller 314. Compression is performed by a high speed compression/decompression FPGA 312, which may perform various levels of lossy compression such as JPEG, MPEG or wavelet, or lossless compression such as RLE. The compressed data is stored in a frame buffer 316 by the compression controller 314. RLE compression, an interframe compression technique, will operate separately on the Y,U, and V components of a single image frame. Other compression techniques such as MPEG and JPEG operate on multiple frames simultaneously. The compressed data is transmitted through a bi-directional FIFO 318 and put on a local bus 320 in four-byte words. The compressed frame data is then transferred to CPU memory by way of a PCI bus 218' by a DMA controller residing in the PCI bridge 324. At this point the frame data is stored on one of the digital storage devices or transmitted or reproduced under control of the CPU 204.

When an image sequence is to be stored without compression the acquisition FPGA controller 304 transmits the image frames directly to biFIFO 330 and onto the local bus 320, from which the image frames are stored under control of the CPU 204. Incoming image sequences may also be processed and then stored or displayed without compression. In this alternative the incoming image frames are transferred from the acquisition FPGA controller 304 to the lookup table 332 and the scalar 334 which can, for example, colorize the images and then scale them to a dual or quad screen format size. The image frames are then transferred by the display FPGA controller 336 to the local bus 320 by way of the biFIFO 330, from which the images can be stored, or to the graphic overlay buffer 340 for transmission by the LVDS transmitter 344 to the ultrasound system for display.

The components of the codec processor are all operated under control of a local processor 322, which transmits control words to the various controllers by way of biFIFOs 318 and 330. The local processor provides realtime control of the various codec operations as commanded by the CPU 204. A memory controller 324 is under control of the local processor and directs control messages through the biFIFOs to the various controllers.

When video data is to be replayed from one of the storage media and displayed, the data retraces its compression path and is decompressed. Under command of the CPU 204 video data retrieved from the storage device and transferred over the PCI bus 218', where it is put on the local bus 320 by the DMA controller residing in the PCI bridge 324. The digital video data on the local bus 320 is coupled to the compression controller 314 by way of the biFIFO 318, under control of the local processor 322. This time the compression controller 314 sends the compressed data to the compression/decompression FPGA 312 where the data is decompressed and the decompressed YUV data is stored in a frame buffer 316. The controller 314 sends the decompressed data to the color space converter 310 where it is reconverted into RGB video. Frames of RGB video are coupled by way of the acquisition FPGA controller 304 to a lookup table 332 which performs operations such as gamma correction and color mapping. The output of the lookup table 332 is coupled to a scalar 334 which performs magnification or minimization of image frames as requested by the user. The frame data is then assembled into a desired display frame format such as full, dual or quad screen in a display frame buffer 338 under control of display FPGA controller 336. The controller 336 synchronizes the previously stored ultrasound image frame to the timing of the ultrasound system's video display processor & D/A 144, so that the user can switch seamlessly back and forth between stored image sequences and live image sequences currently being produced by the ultrasound system. Graphic data is stored in a graphic overlay buffer 340 from which it is synchronized to the timing of the stored ultrasound image frame so that the ultrasound image can be overlaid with graphical information as needed. Stored physiological data such as ECG traces are also synchronized and combined with the ultrasound image in this manner. The graphical and video physic information is retrieved from the storage or transmission medium by the VGA card 208 under control of the CPU 204, is stored in a graphics memory 342, then combined with the ultrasound image frame in the graphic overlay buffer. The final display frame in 24 bit RGB bytes is applied to an LVDS transmitter 344 and then to the video display processor & D/A 144 for display on the display monitor 50.

When uncompressed images are retrieved from storage for display, they retrace the path by which they were stored. Uncompressed image data is transferred by the biFIFO 330 to the acquisition FPGA controller 304, from which it can be colorized or mapped by the lookup table 332, scaled by the scalar 334, and put into the desired display format by the display FPGA controller 336. Alternatively the biFIFO 330 can transfer the image data directly to the display FPGA controller 336 for display.

The codec processor 202 also has the ability to combine stored and live image sequences in a single realtime display frame. A realtime image sequence can be stored on one of the digital storage devices, then retrieved in synchronism with a live realtime image sequence that is currently being produced by the ultrasound system. The retrieved image sequence data is decompressed if necessary, transferred to the acquisition FPGA controller 304, then scaled and formatted by the display FPGA controller for display in one area of a multi-image (dual or quad screen) display. The live image sequence is synchronously transferred by the LVDS receiver 302 to the acquisition FPGA controller 304, then scaled and formatted by the display FPGA controller for display in another area of the multi-image display. The multiimage frame is overlaid with graphic data as needed, then transferred for display on the system display 50 by the LVDS transmitter 344.

The ability of the digital video system 200 to record extended durations of digital ultrasound images approaching that of a VCR is a function of the digital information of an image, the capacity of the digital storage media, and the speed (bandwidth) and performance of the digital processors used, in particular the CPU 204 which mediates the PCI bus. A fourth factor which has a very significant impact on storage capacities is the level of compression selected by the user. In a constructed embodiment an NTSC format image is composed of 480 lines of 640 pixels per line. With each RGB pixel comprising three bytes, a full image is seen to comprise just under one megabyte of data. Using a 200 MHz CPU, the constructed DVS system 200 can store data on a disk drive at rates of 10–17 megabytes per second, which translates to the storage of realtime image sequences having frame rates of 10–15 Hz. This rate for uncompressed images can be increased appreciably through compression. The constructed embodiment performs lossless RLE compression at levels up to 4–6:1, and lossy compression such as JPEG at levels up to 25–30:1. The user is provided choices of lossless, low, medium, or high compression. These choices connote a quality factor of the compressed and then uncompressed images, since the compression is a function of the image data itself and cannot be quantitatively specified with great precision. At these compression levels frame rates of 30 Hz are readily attainable. Storage of five, ten, or twenty minutes of realtime images are possible depending upon the level of compression used. An 8 Gigabyte hard disk can thus store many minutes of realtime images and serve the purpose of a VCR for many echocardiography exams.

Echocardiography images are frequently accompanied by scrolling traces of physiological functions displayed on the ultrasound image display such as a QRS cardiac waveform. To further enable high speed digital storage, the present invention digitizes physiological information such as ECG, pulse and phono signals and transmits the digital data for storage in one of the last lines of the 480 lines of image data, lines which are not used for ultrasonic image display data. Thus, the physiological information is simultaneously stored with the image data to which it relates with no increase in the size of the block of image data. Audio signals such as Doppler sounds which are produced concurrently during imaging are digitized by the sound card 206 and stored in synchronization with the concurrent image data. During replay the digital audio data is routed back over the PCI bus 218 to the sound card, is converted to an analog signal and reproduced through the speakers of the ultrasound system during display of the accompanying image sequence.

Figure 4:
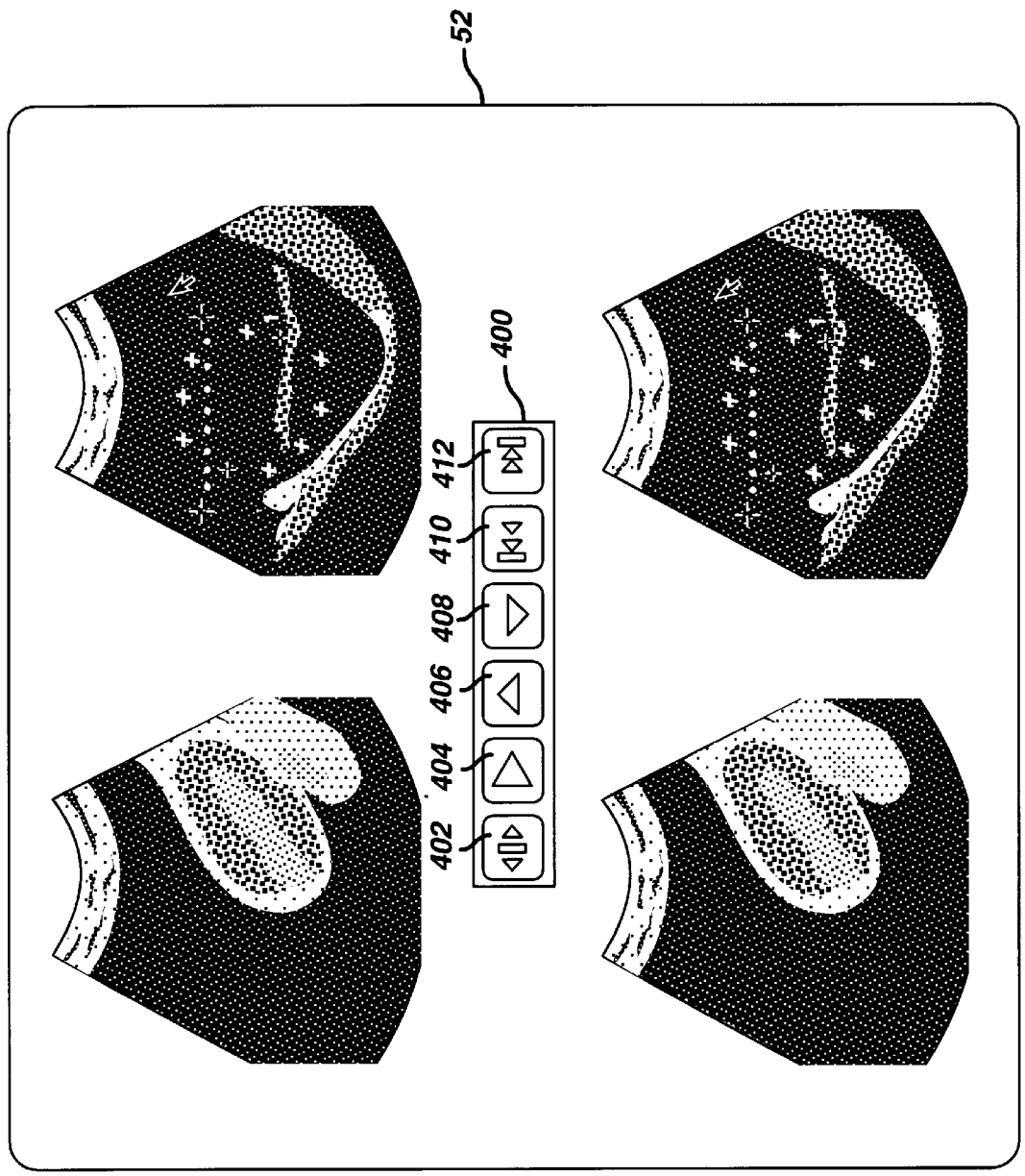
FIG. 4 illustrates a quad screen ultrasound display and the virtual controls of an embodiment of the digital video recorder of the present invention.

FIG. 4 illustrates a quad display as it would appear on a monitor screen 52 when replayed by a digital video storage system of the present invention. Since the present invention can replace the standard VCR, a preferred embodiment uses virtual recorder controls 400 displayed on the monitor screen, which the user would intuitively operate much in the manner of the controls or remote control buttons of a VCR. The virtual buttons of the virtual controls are arranged in a softkey toolbar 400 and take advantage of the versatility of direct digital recording by providing functions not available on the standard VCR. When the user clicks on the first button 402, the user can scan through consecutive frames in an image sequence, one frame at a time. The user can scan through all four image sequences in the quad display simultaneously, or can click on one of the quad images to highlight it and scan through only that sequence of images. In a constructed embodiment the user uses the select key of the ultrasound system's user interface to select a quad display or virtual button, and then uses the trackball of the user interface to scan through the image sequence.

The virtual button 404, when clicked on by the user, plays the image sequences in realtime. When the button 404 is clicked during realtime replay, the realtime display will pause. Repeatedly clicking virtual button 406 will increment the play speed of the images and repeatedly clicking virtual button 408 will decrement the play speed of the images. Virtual buttons 410 and 412 will skip back to a previous mark in a sequence and skip forward to a later mark in the sequence. Marks are placed at points in sequences when long sequences are trimmed to one or more short sequences such as a single cardiac cycle which is of particular interest to a clinician. Such immediate access of points in a sequence of images is not possible with a VCR, since the user must serially advance or rewind the tape to get to other points in a sequence or earlier or later sequences. These virtual buttons enable the user to directly access and instantly replay a trimmed sequence from an editing mark.

It will be appreciated that the softkey control buttons could bear text which describes their functions rather than the graphic symbols as shown in FIG. 4, or that textual descriptions could be programmed to appear when a graphic button is selected. The text would preferably be available in a number of languages so as to be suitable for use in a variety of different countries. However the graphic symbols are preferred as they require no translation and their functions can readily be learned by a user familiar with VCR controls. While the toolbar 400 is shown in the center of the ultrasonic image display in FIG. 4, in a preferred embodiment the toolbar can be positioned by the user at any location on the display screen. A user can thus position the toolbar at the bottom of the screen or at the top of the screen, as desired.

An embodiment of the DVS system of the present invention, with its own CPU and digital storage and response to the user interface of the ultrasound system, can execute stored protocols on the ultrasound system. For instance, the constructed embodiment stores protocols for stress echo exams which are carried out in the following manner. Using the ultrasound system user interface including selections displayed on the monitor, the user selects the desired protocol. The stages to be performed are selected and defined, which for stress echo are the initial rest stage and the post-exercise stage. The views of the heart to be acquired are selected, such as 2D long axis, 2D short axis, apical 4 chamber and apical 2 chamber views. The capture format such as quad screen is selected, and the compression level is chosen. The capture length is also chosen, which can be denominated in time, e.g., 1 second to 5 minutes for each view, or it can be denominated in the number of cardiac cycles or number of images per view. As these choices are made the ultrasound system displays the disk capacity and the number of sequences that can be stored on the selected storage medium at the specified capture length and compression level. Patient images are then acquired one view at a time both pre- and post-stress.

The acquired sequences are then replayed on the display and arranged in the chosen quad format by the display controller 336. The user can edit the image sequences to select out images or heart cycles that are of particular interest. As described above, the user can select one of the four images of the quad display and select the "trim" toolbar. The user can manipulate the trackball to scroll through the full image sequence and mark the first and last frames of portions of a full sequence that are of particular interest. The trimmed sequence can then be stored as a new image sequence. The user can then replay the quad screen display in realtime for only the trimmed sequence intervals, continually replaying the image sequences as image loops.

The versatility a flexibility of the digital recorder makes possible diagnostic tools not previously known. For instance, a quad screen display can be formed from three previously stored image sequences together with one which is just being acquired. Different sequences in a dual or quad screen display can be replayed at different rates at the same time, enabling images of the heart cycle at resting pulse rate to be played in moving synchronism with images of the heart after exercise. The clinician can thus assess the side-by-side performance of the resting and stressed heart with the two realtime sequences of different heart rates apparently moving in synchronism.

What is claimed is:

1. A digital ultrasound video storage system for storing and replaying realtime ultrasonic image sequences comprising:
   a high capacity digital ultrasound image storage medium;
   an image display device;
   a video control; and
   a softkey display, displayed on said image display device and responsive to said video control, for controlling the replay of realtime ultrasonic image sequences from said storage medium.

2. The digital ultrasound video storage system of claim 1, wherein said softkey display comprises a video toolbar including a plurality of virtual controls for said storage system.

3. The digital ultrasound video storage system of claim 2, wherein said virtual controls comprise video buttons.

4. The digital ultrasound video storage system of claim 1, further comprising a digital video controller, responsive to a source of digital ultrasonic images, for controlling the storage of digital ultrasonic images on said high capacity digital ultrasound image storage medium.

5. The digital ultrasound video storage system of claim 1, wherein said softkey display graphically illustrates selectable control functions of said digital ultrasound video storage system.

6. The digital ultrasound video storage system of claim 5, wherein said softkey display graphically illustrates the forward or reverse time direction of replay of a realtime ultrasonic image sequences.

7. The digital ultrasound video storage system of claim 1, wherein said softkey display textually illustrates selectable control functions of said digital ultrasound video storage system.

8. The digital ultrasound video storage system of claim 1, wherein said softkey display comprises a textual softkey display programmable into the language of a country in which said digital ultrasound video storage system is to be used.

9. The digital ultrasound video storage system of claim 1, wherein said video control comprises a video pointer actuatable for visually pointing to a control function of said softkey display.

10. The digital ultrasound video storage system of claim 9, wherein said video pointer comprises the trackball of an ultrasonic diagnostic imaging system.

11. The digital ultrasound video storage system of claim 1, wherein said softkey display comprises a video toolbar which is positionable by a user at a desired location on said image display device.

12. A digital ultrasound video storage system for storing and replaying realtime ultrasonic image sequences comprising:
   a high capacity digital ultrasound image storage medium;
   an image display device;
   a video controller, coupled to the image storage medium and the image display device, which controls the display of stored ultrasound images on the image display device; and
   a plurality of user controls which control at least three of the following functions of ultrasonic image replay:
   a) replay a stored ultrasonic image sequence in realtime,
   b) scan through the frames of an image sequence,
   c) increase the frame rate at which the image sequence is replayed, and d) increase the frame rate at which the image sequence is replayed.

13. The digital ultrasound video storage system of claim 12, wherein said storage medium stores a realtime ultrasonic image sequence which is replayed from storage on said image display device; and wherein said user controls are displayed as a softkey display on said image display device.

14. The digital ultrasound video storage system of claim 13, wherein said realtime ultrasonic image sequence is concurrently displayed along with said softkey display.

15. The digital ultrasound video storage system of claim 12, wherein the functions of ultrasonic image replay further comprise:

e) pausing the realtime replay of an image sequence.

16. The digital ultrasound video storage system of claim 15, wherein the functions of ultrasonic image replay further comprise:

f) skipping forward to a selected ultrasonic image frame, and g) skipping backward to a selected ultrasonic image frame.

17. The digital ultrasound video storage system of claim 16, wherein f) further comprises skipping forward to a marked ultrasonic image frame, and wherein g) further comprises skipping backward to a marked ultrasonic image frame.

18. The digital ultrasound video storage system of claim 12, wherein said image display device displays images of a plurality of ultrasonic image sequences simultaneously and wherein b) further comprises scanning through the frames of a plurality of ultrasonic image sequences simultaneously.

19. The digital ultrasound video storage system of claim 12, wherein the user controls further comprise a textual softkey display programmable into the language of a country in which the digital ultrasound video storage system is to be used.

20. The digital ultrasound video storage system of claim 12, wherein the user controls are grouped to comprise a digital ultrasound video storage system toolbar.

21. A digital ultrasound video storage system for storing and replaying realtime ultrasonic image sequences comprising:

a source of realtime ultrasonic image sequences;

a high capacity digital ultrasound image storage medium;

a storage control for storing and retrieving ultrasonic images from said storage medium;

an image display device;

a video control; and a graphic user interface, responsive to said video control, for controlling the replay of ultrasonic image sequences stored on said storage medium, including graphically denoted softkeys for controlling the speed, direction, starting and stopping of replay of an ultrasonic image sequence on said image display device.

22. The digital ultrasound video storage system of claim 21, wherein said the direction of replay of an image sequence in time is denoted by a triangular symbol pointing in a specified direction.

23. The digital ultrasound video storage system of claim 21, wherein said video control comprises a video pointing device.

24. The digital ultrasound video storage system of claim 23, wherein said video pointing device comprises the trackball of an ultrasonic diagnostic imaging system.

25. The digital ultrasound video storage system of claim 21, wherein said source realtime ultrasonic image sequences comprises an ultrasonic diagnostic imaging system.

26. A digital ultrasound video storage system for storing and replaying realtime ultrasonic image sequences comprising:

a high capacity digital ultrasound image storage medium;

an image display device;

a video controller, coupled to the image storage medium and the image display device, which controls the display of stored ultrasound images on the image display device; and a plurality of user controls which control at least four of the following functions of ultrasonic image replay:

a) replaying a stored ultrasonic image sequence in realtime, b) scanning through the frames of an image sequence, c) increase the frame rate at which the image sequence is replayed, d) decrease the frame rate at which the image sequence is replayed, e) pausing the realtime replay of an image sequence, f) skipping forward to a selected ultrasonic image frame, and g) skipping backward to a selected ultrasonic image frame.

27. The digital ultrasound video storage system of claim 26, wherein the user controls are grouped to comprise a digital ultrasound video storage system toolbar.

28. The digital ultrasound video storage system of claim 27, wherein the toolbar comprises a video toolbar displayed on the image display device.

* * * * *